(12) United States Patent
Niederlöhner et al.

(10) Patent No.: US 9,134,434 B2
(45) Date of Patent: Sep. 15, 2015

(54) X-RAY DETECTOR AND METHOD FOR OPERATING AN X-RAY DETECTOR

(71) Applicant: SIEMENS AKTIENGESELLSCHAFT, Munich (DE)

(72) Inventors: Daniel Niederlöhner, Erlangen (DE); Bodo Reitz, Forchheim (DE); Stefan Wirth, Erlangen (DE)

(73) Assignee: Seimens Aktiengesellschaft, Munich (DE)

( * ) Notice: Subject to any disclaimer, the term of this patent is extended or adjusted under 35 U.S.C. 154(b) by 106 days.

(21) Appl. No.: 13/956,446

(22) Filed: Aug. 1, 2013

(65) Prior Publication Data
US 2014/0042333 A1    Feb. 13, 2014

(30) Foreign Application Priority Data

Aug. 13, 2012  (DE) .......................... 10 2012 214 387

(51) Int. Cl.
*G21K 1/02*     (2006.01)
*G01T 1/17*     (2006.01)
*A61B 6/00*     (2006.01)

(52) U.S. Cl.
CPC ................. *G01T 1/17* (2013.01); *A61B 6/4233* (2013.01); *A61B 6/4291* (2013.01); *G21K 1/025* (2013.01)

(58) Field of Classification Search
CPC ...................................................... G21K 1/025
USPC ......................................................... 378/154
See application file for complete search history.

(56) References Cited

U.S. PATENT DOCUMENTS

| | | | |
|---|---|---|---|
| 6,370,218 B1 | 4/2002 | Toth et al. | |
| 7,156,554 B2 * | 1/2007 | Pfister | 378/207 |
| 2011/0176663 A1 | 7/2011 | Shaughnessy | |

FOREIGN PATENT DOCUMENTS

| | | |
|---|---|---|
| DE | 19650528 A1 | 6/1997 |
| DE | 102008061486 A1 | 2/2010 |
| DE | 102011002505 A1 | 7/2012 |
| WO | WO 2011010995 A1 * | 1/2011 |

* cited by examiner

*Primary Examiner* — Constantine Hannaher
(74) *Attorney, Agent, or Firm* — Harness, Dickey & Pierce (57) ABSTRACT

An x-ray detector for a medical imaging device includes an anti-scatter grid, a measuring layer including a regular arrangement of measuring cells, and an evaluation unit. The anti-scatter grid covers the measuring layer and is aligned toward a specific focal point. The evaluation unit is configured to determine a focal position of an x-ray source relative to the focal point based on a local intensity difference of x-rays striking the measuring layer.

32 Claims, 6 Drawing Sheets

X-RAY DETECTOR AND METHOD FOR OPERATING AN X-RAY DETECTOR

PRIORITY STATEMENT

The present application hereby claims priority under 35 U.S.C. §119 to German patent application number DE 102012214387.4 filed Aug. 13, 2012, the entire contents of which are hereby incorporated herein by reference.

FIELD

At least one embodiment of the invention generally relates to an x-ray detector, in particular for a medical imaging device, including an anti-scatter grid made up of walls, a measuring layer with a regular arrangement of measuring cells and an evaluation unit. At least one embodiment of the invention also generally relates to a method for operating such an x-ray detector.

BACKGROUND

If x-rays are used for an imaging method, these are typically generated in an x-ray tube and in the process irradiated from a relatively small surface to an anode, which, as a good approximation, can be considered as a punctiform x-ray source and is typically referred to as x-ray focus. In order to implement the imaging method, an x-ray detector is also frequently used, which is made up of regularly arranged detector elements or detector pixels.

When examining an object or patient using such a structure comprising an x-ray source and x-ray detector, the attenuation of the x-rays originating from the x-ray source, produced by the object and/or the patient, is generally to be detected directly toward the detector elements, for which reason a so-called anti scatter-grid, which is positioned on the detector elements, is also to be used in many cases.

A corresponding anti-scatter grid is in most instances made up of a plurality of walls, with which a honeycomb-type structure is realized. With the aid of this honeycomb-type structure, x-rays, which do not propagate along a straight connection between the x-ray focus and a detector element, are easily absorbed in the walls of the anti-scatter grid, whereas x-rays, which spread along a straight line between the x-ray focus and a detector element, reach the detector element without a relevant influence by means of the anti-scatter grid. To this end, the walls of the anti-scatter grid and in most instances also the detector elements, are aligned toward the x-ray focus.

Here a change in the focus position defines a change in the positioning of x-ray focus and x-ray detector, including anti-scatter grid, relative to one another, thereby virtually resulting in a misalignment of x-ray source and x-ray detector relative to one another and as a result in a reduction in the image quality which can be achieved using this arrangement. In order to prevent corresponding losses in quality, there is the possibility of either correcting the alignment of x-ray source and x-ray detector relative to one another or preparing the generated image data with the aid of a correction algorithm. In both instances, there is the need here to determine the position of the x-ray focus relative to the x-ray detector and thus also relative to the anti-scatter grid.

In the patent application US 2011/0176663 A1, an apparatus is described, with the aid of which the corresponding x-ray focus position can be determined. Here an anti-scatter grid is used, which is made up of a number of anti-scatter grid modules which are tilted in respect of one another in each instance. The relative alignment of the individual anti-scatter grid modules relative to one another is known and by evaluating the measuring signals of the detector elements assigned to the anti-scatter grid modules, it is determined which of the anti-scatter grid modules is best aligned relative to the x-ray focus.

SUMMARY

At least one embodiment of the invention is directed to to an improved x-ray detector and/or an improved method for operating an x-ray detector.

An x-ray detector of an embodiment of the invention is disclosed. The related claims contain in part advantageous and in part per se inventive developments of embodiments of the invention.

The x-ray detector of an embodiment is provided for a medical imaging device, such as a computed tomography system, and includes a anti-scatter grid made up of walls, a measuring layer with a regular arrangement of measuring cells and an evaluation unit. Here the anti-scatter grid completely covers the measuring layer, as a good approximation, and is preferably aligned, together with the measuring layer, with a specific focus point. In addition, the evaluation unit is set up such that this determines a focal position of an x-ray source relative to the focal point based on a local intensity difference of x-rays striking the measuring layer.

An embodiment of an improved method for operation of an x-ray detector is also disclosed.

The method of an embodiment is used to operate an x-ray detector, in particular an x-ray detector of the type described previously, wherein the x-ray detector includes an anti-scatter grid made up of walls, a measuring layer with a regular arrangement of measuring cells and an evaluation unit. Within the scope of an embodiment of the method, a focal position of an x-ray source is determined relative to a specific focal point, toward which the anti-scatter grid is aligned, based on a local intensity difference of x-rays striking the measuring layer. To this end, the measuring signals generated by means of the measuring layer are evaluated, said measuring signals preferably being generated while an examination object or patient is positioned between the x-ray source and the anti-scatter grid.

BRIEF DESCRIPTION OF THE DRAWINGS

Example embodiments of the invention are explained in greater detail below on the basis of a schematic drawing, in which.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An x-ray detector of an embodiment of the invention is disclosed. The related claims contain in part advantageous and in part per se inventive developments of embodiments of the invention.

The x-ray detector of an embodiment is provided for a medical imaging device, such as a computed tomography system, and includes a anti-scatter grid made up of walls, a measuring layer with a regular arrangement of measuring cells and an evaluation unit. Here the anti-scatter grid completely covers the measuring layer, as a good approximation, and is preferably aligned, together with the measuring layer, with a specific focus point. In addition, the evaluation unit is set up such that this determines a focal position of an x-ray source relative to the focal point based on a local intensity difference of x-rays striking the measuring layer.

The focal position is determined in this case by the evaluation unit, by assuming that an x-ray source is assigned to the x-ray detector during operation and is used in an arrangement together herewith for an imaging method. That x-ray source can herewith be considered to be a punctiform x-ray source, as a good approximation, the position of which is subsequently referred to as focal position. This focal position, in other words the position of the punctiform x-ray source, is monitored during operation of the x-ray detector or is determined at least in specific operating states.

It is further assumed that depending on the position of the punctiform source, in other words depending on the focal position, a differently sized portion of the unscattered x-rays is absorbed by the walls of the anti-scatter grid. This is because of the formation of a shadow on the measuring layer caused by the walls, wherein the extent of the shadow depends on the focus position. Consequently, local intensity differences are then caused by x-rays striking the measuring layer, which eventually also results in local differences in the measuring signals generated by the measuring layer. At least one wall is therefore used in principle, in order to realize a type of sun dial, with which the position of the punctiform x-ray source, which acts here almost like the sun, is determined.

In the simplest case, provision is made in at least one embodiment to determine differences between intensities detected by individual measuring cells in order to determine the focal position. The measuring signals of two adjacent measuring cells which are separated by a wall are therefore related to one another for instance, from which it is then possible to determine the angle at which the unscattered x-rays emitted from the punctiform x-ray source strike this wall. If it is also assumed for instance with a computed tomography system that the focal position only moves on a cylinder surface or a spherical surface without leaving this surface, the relative position of the punctiform x-ray source, in other words the focal position, relative to the x-ray detector and thus also to the anti-scatter grid can be calculated from this information.

The focal point is used here as a reference point for the focal position, the focal point being predetermined by the structure of the x-ray detector and by the position of the same in an arrangement comprising x-ray source and x-ray detector. If a punctiform x-ray source is positioned on this focal point, the x-ray source and x-ray detector are aligned relative to one another. In the event of a measuring layer which is embodied to be flat, the focal point lies for instance on a straight line, which runs through the center of gravity of the surface of the measuring layer and in parallel to the surface normal. Also widespread are x-ray detectors having a measuring layer with a curved surface, wherein the focal point thereof corresponds to the peak of a straight cone so that the surface of the measuring layer is provided by a conical intersection, the points of which have a uniform distance from the focal point. With an x-ray detector embodied in this way, the anti-scatter grid also frequently has a layout which is adjusted thereto, wherein the walls run along the boundaries between measuring cells of the measuring layer and also extend in the direction of the focal point.

In accordance with a preferred embodiment variant of the x-ray detector, the walls of the anti-scatter grid delimit each measuring cell and thus define the useful surface of the measuring cells. The measuring cells are further preferably designed to be rectangular or square here and are enclosed in particular by four walls, wherein the selected wall strength of the walls defines how large the surface is, which is covered by the walls on the measuring layer and thus also how large the remaining surface of each measuring cell framed by four walls is respectively, said measuring cell herewith being used as a useful surface for detecting x-rays using measuring techniques. The measuring cells are formed here by a number of regularly arranged sensor pixels or an individual sensor pixel forms an individual sensor cell.

Furthermore, the anti-scatter grid preferably comprises a first type of wall and a second type of wall which differs therefrom, wherein that anti-scatter grid is further preferably predominantly made up of walls of the first type and comprises detached walls of the second type. The use of differently embodied walls is then particularly advantageous if not all measuring cells of the measuring layer or rather the measuring signals thereof are used to determine the focal position. In this case, walls in the region of the measuring cells, the signals of which are used to determine the focal position, are configured such that on account of their form, the appearance of local intensity differences of x-rays striking the measuring layer is favored, whereas the remaining walls are preferably designed such that smaller deviations in the focal position from the focal point produce as far as possible no reduction in the image quality which can be achieved with the arrangement comprising x-ray source and x-ray detector. In other words, only a few measuring cells are preferably used to determine the focal position, whereas all measuring cells are used for image generation within the scope of the imaging method.

It is advantageous here if the first type of walls has a basic wall strength and in the region bordering the measuring layer has a first base wall strength, which is larger by comparison with the basic wall strength. An embodiment of the second type of walls is furthermore advantageous, in which these walls have a basic wall strength and in the region bordering the measuring layer have a second base wall strength which is lower by comparison with the first base wall strength and which further preferably corresponds to the basic wall strength.

On account of the first base wall strength of the first type of wall which is increased by comparison with the basic wall strength, a larger surface of the measuring cells is covered by these walls. This region which is also covered on account of the increase in the wall strength corresponds somewhat to the region on which a shadow develops with a correspondingly slight variation in the focal position. Since this region is nevertheless permanently covered on account of the increased first base wall strength and thus does not contribute to the measuring signal generation, correspondingly more slight variations in the focal positions have no negative affect on the generation of the measuring signals of the corresponding measuring cells. It is precisely this negative, actually unwanted influence that is used in an x-ray detector presented here, in order to determine the focal position, as a result of which walls of the second type are positioned at least in individual subareas on the measuring layer, the second base wall strength of which is smaller than the first base wall strength.

In addition, particularly adjacent measuring cells, the measuring signals of which are used to determine the focal position, are separated by walls of the second type and further preferably each measuring cell, the measuring signals of which are used to determine the focal position, is delimited or even enclosed by walls of the anti-scatter grid which are configured differently. In the simplest case, the anti-scatter grid only comprises a single wall of the second type, which separates two adjacent measuring cells from one another and only the measuring signals of these two measuring cells are evaluated in order to determine the focal position. In this variant, changes to the focal position can be determined provided the punctiform x-ray source moves along a simple path. If more complex movements of the punctiform x-ray source are possible, the measuring signals from a larger number of measuring cells are used to determine the focal position and the anti-scatter grid comprises a larger number of walls of the second type. Here the walls of the second type are advantageously arranged along not only one but instead two directions which run orthogonally relative to one another.

The determination of the focal position can in principle take place within the scope of a calibration process, the focal position is nevertheless preferably determined during each image-generating process, in other words while an examination object or a patient is positioned between the x-ray source and the anti-scatter grid. It is advantageous, precisely in this case, if each measuring cell is provided by an individual sensor pixel, since, in this case, on the basis of a typical extent of a sensor pixel of 1 mm×1 mm in a good approximation, it can be assumed that the intensity differences of x-rays striking the measuring layer between two adjacent sensor pixels is less through the examination object than instead through the position of the punctiform x-ray source.

The determined focal position is also preferably stored, or at least buffered, together with the generated measuring signals in order to take this into account for instance with the post-processing of the measuring signals. Provision is made here for instance, based on the measuring data, to generate image data and to post-process the same using an algorithm.

An embodiment of an improved method for operation of an x-ray detector is also disclosed.

The method of an embodiment is used to operate an x-ray detector, in particular an x-ray detector of the type described previously, wherein the x-ray detector includes an anti-scatter grid made up of walls, a measuring layer with a regular arrangement of measuring cells and an evaluation unit. Within the scope of an embodiment of the method, a focal position of an x-ray source is determined relative to a specific focal point, toward which the anti-scatter grid is aligned, based on a local intensity difference of x-rays striking the measuring layer. To this end, the measuring signals generated by means of the measuring layer are evaluated, said measuring signals preferably being generated while an examination object or patient is positioned between the x-ray source and the anti-scatter grid.

Figure 1:
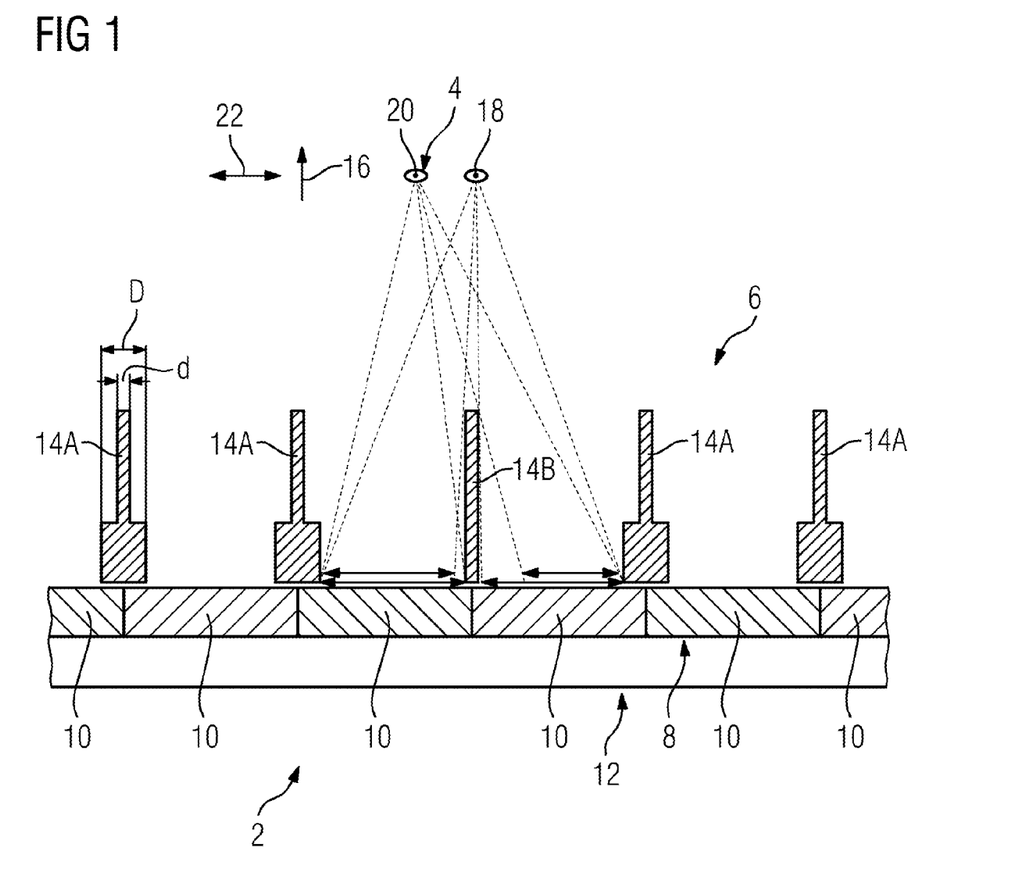
FIG. 1 shows a sectional representation in part of an arrangement comprising x-ray source and x-ray detector.

The x-ray detector 2 described by way of example below is, similarly to an x-ray source 4, part of an computed tomography system, which is used to examine an object or patient using an imaging method which is known per se. In such a computed tomography system, the x-ray detector 2 and x-ray source 4, as indicated in FIG. 1, are arranged opposite one another and in order to examine the object and/or patient, this is positioned on an examination couch (not shown), which is positioned between the x-ray detector 2 and the x-ray source 4.

The generation of the x-rays takes place by way of an x-ray tube (not shown), in which the generation of the x-rays on a relatively small region of an anode, the so-called focal spot, is delimited. This focal spot then acts in a good approximation as a punctiform x-ray source 4, which is represented in FIG. 1 by the image of the focal spot. Starting from the x-ray source 4, the x-rays spread in a conical manner in the direction of the x-ray detector 2, wherein this, at least provided an object to be examined or a patient to be examined is introduced into the radiation cone, firstly strikes the object and/or patient to be examined. Part of the x-ray is absorbed in this process in the object or patient, while the transmitted part of the x-ray subsequently strikes the x-ray detector 2. A further part is scattered by interaction with the object and/or patient, wherein this part tends to be disadvantageous for the imaging method.

For this reason, the x-ray detector 2 comprises an anti-scatter grid 6, with the aid of which a large part of the scattered x-rays is absorbed. By contrast, the unscattered x-rays, which are transmitted through the object and/or the patient, pass through the anti-scatter grid 6 essentially unaffected to a measuring layer 8, which is made up of a regular arrangement of measuring cells 10 and is detected there using measuring techniques. A measuring signal is generated here in each measuring cell 10 as a function of the intensity of the x-rays striking this measuring cell 10, said measuring signal being fed to an evaluation unit 12 for further processing.

The anti-scatter grid 6 is made up of two walls 14 which are embodied differently, said walls being aligned in the direction of the surface normal 16 (in the event of a curved measuring layer and a curved anti-scatter grid in the direction of the focal point and thus typically only approximately in the direction of the surface normal) of the measuring layer 8 and run along the boundaries between the measuring cells 10. Accordingly, each rectangular measuring cell 10 in the exemplary embodiment is enclosed by four walls. A first type of wall A herewith comprises in the region of the measuring layer 8 a first base wall strength D which is increased by comparison with a basic wall strength d, while the second type of wall B comprises a uniform wall strength 16 across the entire extent in the direction of the surface normal 16, said wall strength 16 corresponding to the basic wall strength d.

A focal point 18 is assigned to the x-ray detector 2, on which the positioning of the punctiform x-ray source 4 is provided, so as to achieve as favorable as possible an interaction between the x-ray source 4 and the x-ray detector 2 within the scope of the imaging method. This focal point 18 results from the structure of the x-ray detector 2, wherein, in the present case here, the focal point 18 lies on a straight line through the center of gravity of the surface of the measuring layer 8, which runs along the surface normal 16.

With a likewise typical embodiment of an x-ray detector with a curved surface of the measuring layer, the walls of the anti-scatter grid are aligned in the manner of a fan relative to one another and in each instance relative to a shared point, which then forms the focal point of this x-ray detector. Each point on the surface of the measuring layer is then equidistant from this focal point.

The evaluation unit 12 of the x-ray detector 2 is further configured such that the position of the punctiform x-ray source 4, subsequently referred to as focal position 20, is monitored relative to the focal point 18. The focal position 20 is determined here by evaluating the measuring signals of two adjacent measuring cells 10, which are arranged centrally in the measuring layer 8 and are separated from one another by a wall 14 of the second type B. During the evaluation, the intensities of the x-rays striking these two measuring cells 10 which were detected using measuring techniques are related to one another in order therefrom to determine a local intensity difference, from which, in accordance with the principle of a sun dial, it is possible to conclude the focal position 20 relative to the focal point 18. It is assumed here in simplified terms that the x-ray source 4 does not move in the direction of the surface normal 16 but instead only at right angles thereto and in particular only in a Phi direction 22.

According to the diagram in FIG. 1, the two measuring cells 10 separated by the wall 14 of the second type B are essentially illuminated in an identical manner during irradiation using x-rays from the focal point 18, whereas with an irradiation of these two measuring cells 10 from a deviating focal position 20, a shading of one of the two measuring cells 10 takes place by the wall 14 between the two measuring cells 10, so that the intensity of the x-rays striking these measuring cell 10 compared with an irradiation from the focal point 18 is reduced, thereby resulting in detection of different intensities by means of the two adjacent measuring cells 10.

Since intensity differences of this type, which are caused by a focal position 20 deviating from the focal point 18, are disadvantageous for the image quality which can be achieved by means of the arrangement, provision is made for the x-ray detector 2 for an anti-scatter grid 6 with just one wall 14 of the second type B, while the remaining walls 14 have a layout of the first type A. The walls 14 of the first type A are provided with a strengthened wall, the first base wall strength D, in the region of the measuring layer 8, so that in the border region of the measuring cells 10, these permanently cover part of the maximum useful surface of the measuring cells 10, in other words the surface which can be used to detect x-rays using measuring techniques in the absence of an anti-scatter grid 6, so that this covered region is not used to detect x-rays using measuring techniques. In precisely this region, a shadow develops in the event of a slight displacement of the focal position 20 with respect to the focal point 18, said shadow, in the event of using walls 14 of the second type B, possibly resulting in an intensity difference of adjacent measuring cells 10. This region is nevertheless permanently covered on account of the use of walls 14 of the first type A, so that with a slight displacement of the focal position 20 with respect of the focal point 18, no or only minimal intensity differences in the measuring cells 10 are detected.

Embodiment variants of the x-ray detector 2 are generally preferred here, in which the majority of measuring cells 10 are delimited by walls 14, with which the formation of a shadow in the measuring cells 10 on account of a slight deviation in the focal position 20 from focal position 18 is faded out by the partial coverage of the measuring cells 10 by means of the walls 14 and is thus not detected using measuring techniques and in which only a few walls 14 are used, which are embodied such that a clear formation of shadow and thus a clear influencing of the measuring signals is produced by a focal position 20 which deviates from the focal point 18. The few measuring cells 10 bordering these walls 14 are then used to determine and/or monitor the focal position 20 based on its measuring signals, as a result of which preferably all measuring cells 10 are used to obtain measuring signals for the generation of image data.

Figure 2:
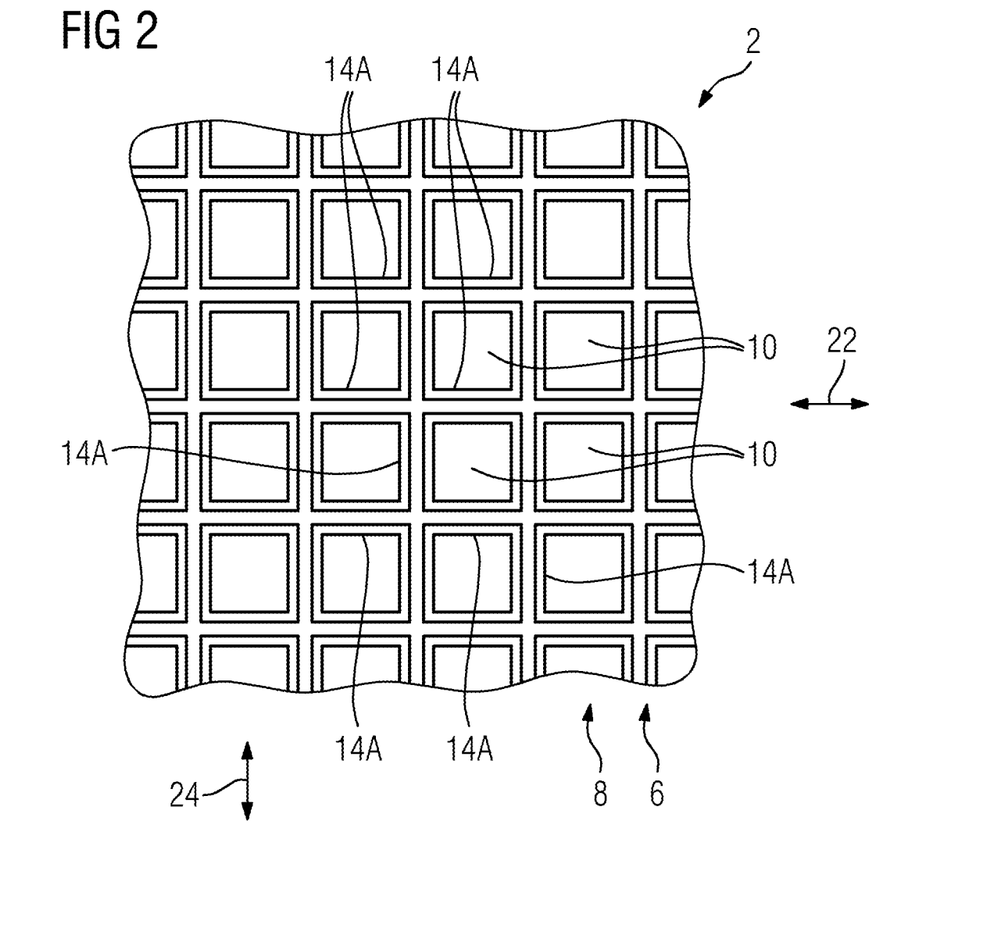
FIG. 2 shows a top view onto a first cut-out of the x-ray detector.
Figure 3:
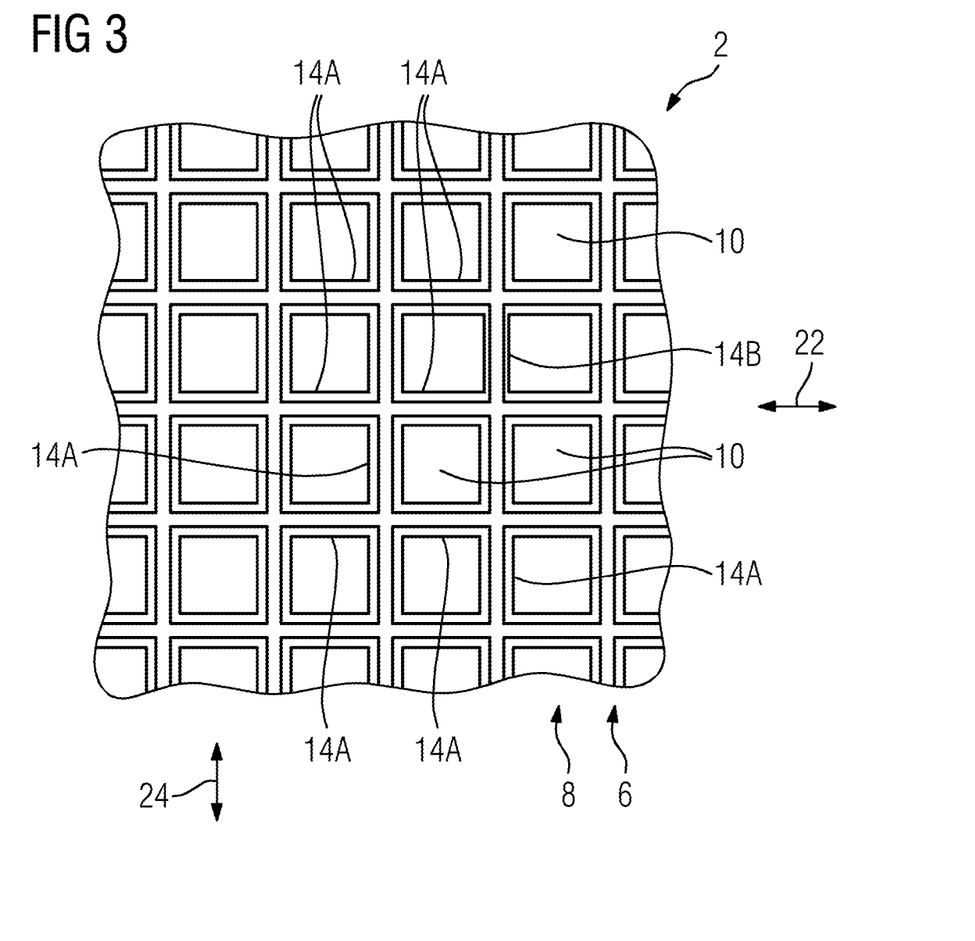
FIG. 3 shows a top view onto a second cut-out of the x-ray detector.

Different alternative embodiment variants of the x-ray detector 2, or in more precise terms of the anti-scatter grid 6, are shown in the images FIG. 3 to FIG. 6, wherein in all these instances, the anti-scatter grid 6 is predominantly made up of walls 14 of the first type A and accordingly has a layout as shown in FIG. 02 across large regions. Individual walls are nevertheless present in the anti-scatter grid 6 in order to determine the focal position 20, said walls in the region of the measuring layer 8 having a reduced wall strength by comparison with the first base wall strength D, as indicated in FIG. 3, or nevertheless having a uniform wall strength across the entire extent in the direction of the surface normal 16, which, such as in the exemplary embodiment from FIG. 1, corresponds to the base wall strength d.

Figure 4:
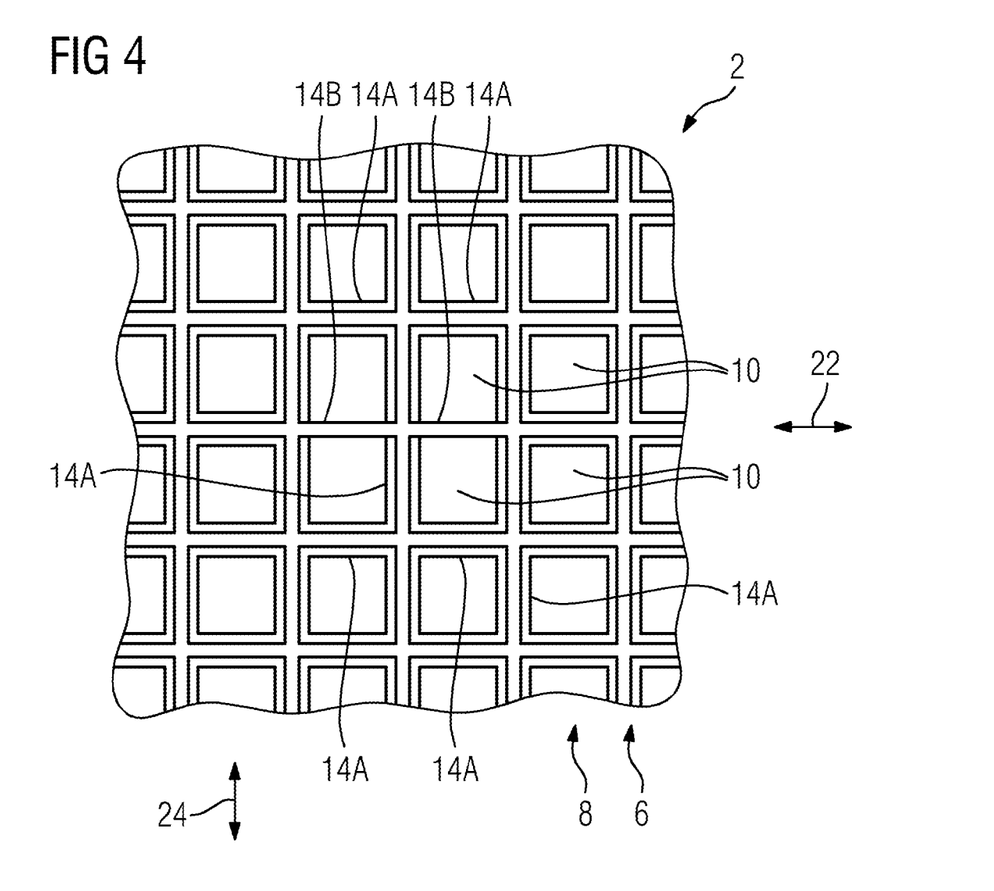
FIG. 4 shows a top view onto a cut-out of a first alternative x-ray detector.
Figure 5:
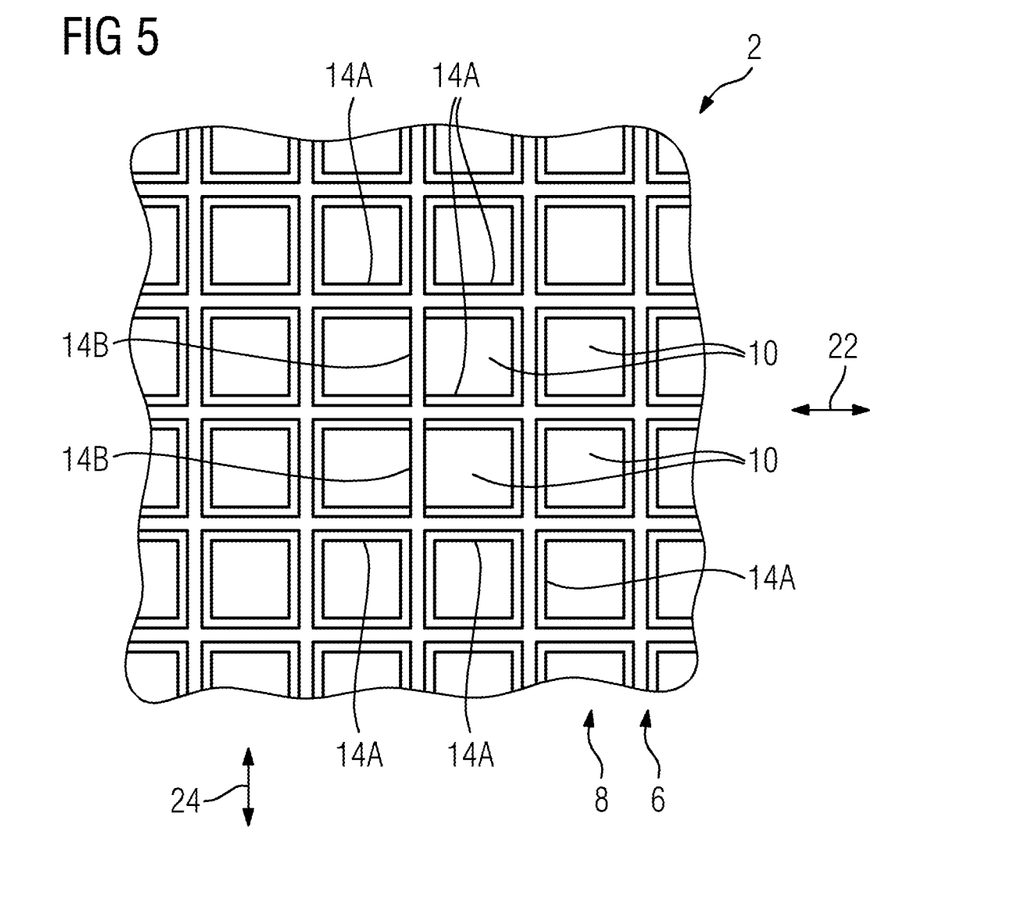
FIG. 5 shows a top view onto a cut-out of a second alternative x-ray detector and FIG. 6 shows a top view onto a cut-out of a third alternative x-ray detector, Parts corresponding to one another are labeled with the same reference numerals in all the figures.
Figure 6:
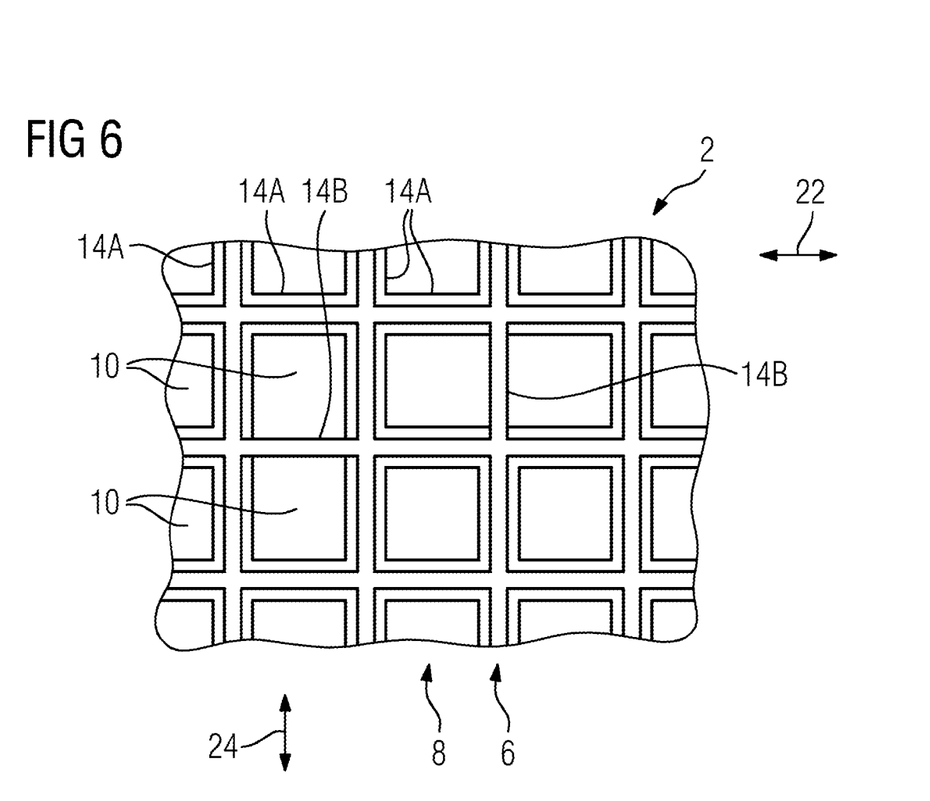

With a computed tomography system, an x-ray detector 2 is frequently used, the measuring cells 10 of which together embody a cylinder partial surface and in this way, based on cylinder coordinates, are arranged along the Phi direction 22 on the one hand and the z-direction 24 on the other hand. In this case, walls 14 of the second type B are to be aligned in parallel to the Phi direction 22, as shown in FIG. 4, or as shown in FIG. 5, are to be aligned in parallel to the z-direction 24 for instance. In both instances, a deviation in the focal position 20 from the focal point 18 can be determined in one of these two directions 22, 24. If nevertheless a position deviation is detected in two orthogonal directions 22,24, walls 14 of the second type B, as shown in FIG. 6, are to be arranged along two orthogonal directions 22,24.

The number of measuring cells 10 used to determine the focal position 20 is preferably restricted to a few, wherein these are not imperatively arranged in rows adjacent to one another, but instead may also be arranged in individual clusters, which are then spatially separate from one another.

The invention is not limited to the example embodiment described hereintofore. Rather, other variants of the invention can also be derived herefrom by the person skilled in the art, without departing from the subject matter of the invention. In particular it is furthermore possible to combine all the individual features described in connection with the exemplary embodiment with one another in a different way also, without departing from the subject matter of the invention.

What is claimed is:

1. An x-ray detector, comprising:
   an anti-scatter grid;
   a measuring layer including an arrangement of measuring cells, the anti-scatter grid covering the measuring layer and being aligned at a focal point; and
   an evaluation unit, configured to determine a focal position of an x-ray source relative to the focal point based on differences between respective local intensities detected by individual ones of only a portion of the measuring cells, the respective local intensities being intensities of x-rays incident on the measuring layer.

2. The x-ray detector of claim 1, wherein
   the anti-scatter grid includes walls; and
   respective walls of the anti-scatter grid delimit respective measuring cells and define a useful surface.

3. The x-ray detector of claim 2, wherein each measuring cell from among the individual ones of the portion of the measuring cells is delimited by differently configured walls of the anti-scatter grid.

4. The x-ray detector of claim 3, wherein
   the evaluation unit is configured to determine the focal position based on measuring signals generated by the individual ones of only the portion of the measuring cells, the measuring signals being generated based on the respective local intensities detected by the individual ones of only the portion of the measuring cells; and
   an examination object is positioned between the x-ray source and the anti-scatter grid.

5. The x-ray detector of claim 2, wherein the anti-scatter grid includes a first type of walls and a second type of walls, the second type of walls being configured different from the first type of walls.

6. The x-ray detector of claim 5, wherein the anti-scatter grid is substantially made up of walls of the first type and comprises detached walls of the second type.

7. The x-ray detector of claim 6, wherein the first type of walls includes a basic wall strength and, in a region bordering the measuring layer, includes a first base wall strength, which is larger than the basic wall strength.

8. The x-ray detector of claim 7, wherein the second type of walls includes the basic wall strength and, in the region bordering the measuring layer, includes a second base wall strength, which is smaller than the first base wall strength.

9. The x-ray detector of claim 5, wherein the first type of walls includes a basic wall strength and, in a region bordering the measuring layer, includes a first base wall strength, which is larger than the basic wall strength.

10. The x-ray detector of claim 9, wherein the second type of walls includes the basic wall strength and, in the region bordering the measuring layer, includes a second base wall strength, which is smaller than the first base wall strength.

11. The x-ray detector of claim 5, wherein adjacent measuring cells from among the individual ones of the portion of the measuring cells are separated by walls of the second type.

12. A medical imaging device comprising the x-ray detector of claim 2.

13. The x-ray detector of claim 1, wherein the anti-scatter grid includes a first type of walls and a second type of walls, the second type of walls being configured different from the first type of walls.

14. The x-ray detector of claim 13, wherein the anti-scatter grid is substantially made up of walls of the first type and comprises detached walls of the second type.

15. The x-ray detector of claim 14, wherein the first type of walls includes a basic wall strength and, in a region bordering the measuring layer, includes a first base wall strength, which is larger than the basic wall strength.

16. The x-ray detector of claim 15, wherein the second type of walls includes the basic wall strength and, in the region bordering the measuring layer, includes a second base wall strength, which is smaller than the first base wall strength.

17. The x-ray detector of claim 14, wherein adjacent measuring cells from among the individual ones of the portion of the measuring cells are separated by walls of the second type.

18. The x-ray detector of claim 14, wherein each measuring cell from among the individual ones of the portion of the measuring cells is delimited by differently configured walls of the anti-scatter grid.

19. The x-ray detector of claim 13, wherein the first type of walls includes a basic wall strength and, in a region bordering the measuring layer, includes a first base wall strength, which is larger than the basic wall strength.

20. The x-ray detector of claim 19, wherein the second type of walls includes the basic wall strength and, in the region bordering the measuring layer, includes a second base wall strength, which is smaller than the first base wall strength.

21. The x-ray detector of claim 20, wherein the second base wall strength corresponds to the basic wall strength.

22. The x-ray detector of claim 13, wherein adjacent measuring cells from among the individual ones of the portion of the measuring cells are separated by walls of the second type.

23. The x-ray detector of claim 13, wherein each measuring cell from among the individual ones of the portion of the measuring cells is delimited by differently configured walls of the anti-scatter grid.

24. A medical imaging device comprising the x-ray detector of claim 13.

25. The x-ray detector of claim 1, wherein the x-ray detector is for a medical imaging device.

26. A medical imaging device comprising the x-ray detector of claim 1.

27. A method for operating the x-ray detector of claim 1, the method comprising:
   determining the focal position of the x-ray source relative to the focal point, toward which the anti-scatter grid is aligned, based on the differences between the respective local intensities detected by the individual ones of only the portion of the measuring cells.

28. The method of claim 27, wherein an examination object is positioned between the x-ray source and the anti-scatter grid.

29. The x-ray detector of claim 1, wherein
   the individual ones of only the portion of the measuring cells include at least a first measuring cell and a second measuring cell separated by a wall; and
   the evaluation unit is further configured to
      determine an angle at which unscattered x-rays emitted from the x-ray source strike the wall based on the differences between the respective local intensities, and
      determine the focal position of the x-ray source relative to the focal point based on the determined angle at which the unscattered x-rays strike the wall.

30. A method for operating an x-ray detector including an anti-scatter grid, a measuring layer including an arrangement of measuring cells and an evaluation unit, the method comprising:
   determining a focal position of an x-ray source relative to a focal point, toward which the anti-scatter grid is aligned, based on differences between respective local intensities detected by individual ones of only a portion of the measuring cells, the respective local intensities being intensities of x-rays incident on the measuring layer.

31. The method of claim 30, wherein an examination object is positioned between the x-ray source and the anti-scatter grid.

32. The method of claim 30, wherein the individual ones of only the portion of the measuring cells include at least a first measuring cell and a second measuring cell separated by a wall, and wherein the determining comprises:
   determining an angle at which unscattered x-rays emitted from the x-ray source strike the wall based on the differences between the respective local intensities; and
   determining the focal position of the x-ray source relative to the focal point based on the determined angle at which the unscattered x-rays strike the wall.

\* \* \* \* \*